United States Patent
Graessner

(10) Patent No.: US 7,206,629 B2
(45) Date of Patent: Apr. 17, 2007

(54) METHOD FOR IMPLEMENTING A DYNAMIC MAGNETIC RESONANCE MEASUREMENT WITH THE APPLICATION OF A CONTRAST AGENT

(75) Inventor: Joachim Graessner, Bönningstedt (DE)

(73) Assignee: Siemens Aktiengesellschaft, Munich (DE)

( * ) Notice: Subject to any disclaimer, the term of this patent is extended or adjusted under 35 U.S.C. 154(b) by 617 days.

(21) Appl. No.: 10/338,255

(22) Filed: Jan. 8, 2003

(65) Prior Publication Data

US 2003/0176782 A1 Sep. 18, 2003

(30) Foreign Application Priority Data

Jan. 8, 2002 (DE) ................ 102 00 371

(51) Int. Cl.
*A61B 5/05* (2006.01)
(52) U.S. Cl. ............... 600/420; 600/431; 600/410
(58) Field of Classification Search ............... 600/410, 600/420, 421, 431
See application file for complete search history.

(56) References Cited

U.S. PATENT DOCUMENTS

| | | | | |
|---|---|---|---|---|
| 5,908,386 | A * | 6/1999 | Ugurbil et al. ............ | 600/410 |
| 6,205,349 | B1 * | 3/2001 | Kim et al. ................. | 600/420 |
| 6,295,465 | B1 | 9/2001 | Simonetti | |
| 2003/0042905 | A1 * | 3/2003 | Miyazaki et al. .......... | 324/314 |

OTHER PUBLICATIONS

"Fettunterdrückende STIR-Sequenzen mit und ohne Kontrastmittel bei der MRT von HNO-Tumoren," (Fat-Suppressed STIR Sequences With and Without Contrast Medium in MRT of ENT Tumors), Brüning et al. Fortschr:Röntgenstr. vol. 160, No. 5 (1994) pp. 412-416.

"T1-Relaxation Kinetics of Extracellular, Intracellular and Intravascular MR Contrast Agents In Normal And Acutely Reperfused Infarcted Myocardium Using Echo-Planar MR Imaging," Saeed et al., Eur. Radiol., vol. 10, (2000) pp. 310-318.

"Inversion Recovery EPI of Bolus Transit in Rat Myocardium Using Intravascular and Extravascular Gadolinium-Based MR Contrast Media: Dose Effects on Peak Signal Enhancement," Wendland et al., Magnetic Resonance in Medicine, vol. 32, No. 3 (Sep. 1994), pp. 319-329.

\* cited by examiner

*Primary Examiner*—Brian L. Casler
*Assistant Examiner*—Jacqueline Cheng
(74) *Attorney, Agent, or Firm*—Schiff Hardin LLP

(57) ABSTRACT

In a method for implementing a dynamic magnetic resonance measurement with contrast agent administration, at least one imaging magnetic resonance measurement of a subject region is implemented using an inversion recovery sequence at a first and possibly further points in time after administration of the contrast agent, to obtain a magnetic resonance image of the subject region. Immediately before the first and, if used, the further points in time, a pre-measurement with a magnetic resonance sequence is implemented wherein the T1 time of a tissue type, or a substance type that is of no interest in the magnetic resonance image of the subject region, is determined, and an inversion time TI used for the following imaging magnetic resonance measurement is calculated as TI=ln2 ×T1.

6 Claims, 2 Drawing Sheets

METHOD FOR IMPLEMENTING A DYNAMIC MAGNETIC RESONANCE MEASUREMENT WITH THE APPLICATION OF A CONTRAST AGENT

CROSS-REFERENCE TO RELATED APPLICATION

The present application claims priority to German application No. 10200371.8 filed Jan. 8, 2002.

BACKGROUND OF THE INVENTION

1. Field of the Invention

The present invention is directed to a method for the implementation of a dynamic magnetic resonance measurement with a contrast agent, of the type wherein at least one imaging magnetic resonance measurement of a subject region is implemented using an inversion recovery sequence at a first point in time and possibly further points in time, after administration of the contrast agent in order to obtain a magnetic resonance image of the subject region.

2. Description of the Prior Art

Magnetic resonance tomography is a known technique for acquiring images of the inside of the body of a living examination subject. For implementation of magnetic resonance tomography, a basic field magnet generates a static, relatively uniform basic magnetic field. Rapidly switched gradient fields that are generated by as gradient coils are superimposed on this basic magnetic field during the exposure of magnetic resonance images. Radiofrequency pulse sequences are emitted into the examination subject with radiofrequency transmission antennas for triggering magnetic resonance signals that are picked up by radiofrequency reception antennas. Magnetic resonance images with different weightings of individual tissue types or substance types of the subject region of interest can be generated with different pulse sequences.

A field of magnetic resonance tomography relates to dynamic magnetic resonance measurements with the use of contrast agents. Vitality (viability) examinations at the heart after a heart attack or a surgical intervention at the heart is one example of this field. The contrast agent injected into the patient causes a temporary modification of the T1 times, i.e. the longitudinal relaxation times, of the tissue. A viability examination exploits the fact healthy tissue (with blood circulation) absorbs the contrast agent quickly and also releases it quickly, whereas the contrast agent increases in concentration relatively slowly in dead tissue. In a dynamic measurement, a waiting time of, for example, 5 minutes is therefore introduced after injection of the contrast agent before a first imaging magnetic resonance measurement of the subject region of interest is implemented. As a rule, a number of such measurements are implemented at further time intervals, so that the so-called late enhancement in dead tissue regions can be observed on the basis of the magnetic resonance images produced at different points in time. Dynamic magnetic resonance measurement with the application of contrast agent thus enables the identification of dead tissue regions affected by the cardiac infarction that can no longer be revitalized by means of a surgical intervention. The success of a surgical intervention, for example a percutaneous transluminal coronary angioplasty (PTCA) or a coronary bypass operation (CABG), also can be reviewed in this way.

Fast gradient echo sequences are utilized in these measurements in order to avoid motion artifacts. A technique known as the inversion recovery technique can be utilized for generating high-contrast magnetic resonance (MR) images, wherein the longitudinal magnetization is inverted with a 180° pulse and interrogated with a further RF pulse after an inversion time T1. The inversion of the longitudinal magnetization by the 180° pulse also is referred to as a preparation phase for the measurement. The inversion time T1 represents a significant factor for the generation of high-contrast MR images. With a suitable selection of this inversion time, the healthy muscle tissue (myocardium) appears dark in the MR image, whereas the region enhanced with contrast agent are displayed light (bright). Due to the time intervals between the individual measurements, however, the T1 times of the healthy muscle tissue change because the contrast agent is flushed out, so that a different T1 time must be employed for an optimum contrast at each measurement time of the dynamic measurement.

The selection of suitable T1 times conventionally has been based on empirical data. The T1 time is therefore iteratively adapted from measurement time to measurement time over the course of the examination. Conventionally, the T1 time has to be followed-up according to the empirical values given repetitive repetitions of such measurements, for example, up to a time of 300 ms in steps beginning with a start value of T1=260 ms for the myocardium suppression. This empirical T1 selection, however, does not always achieve an optimum contrast with a suppression of healthy muscle tissue in the MR image of the heart on a case-by-case basis.

SUMMARY OF THE INVENTION

An object of the present invention is to provide a method for the implementation of a dynamic magnetic resonance measurement with the application of a contrast agent with which an optimum suppression of a prescribable tissue type or substance type can be achieved at any time for achieving an optimum contrast.

This object is achieved in accordance with the invention in a method for the implementation of a dynamic magnetic resonance measurement with the application of a contrast agent, at least one imaging magnetic resonance measurement of a subject region is implemented using an inversion recovery sequence at a first and possibly further points in time after administration of the contrast agent in order to obtain a magnetic resonance image of the subject region, wherein immediately before each of the first and, (if used) the further points in time, a pre-measurement with a magnetic resonance sequence is implemented for determining the T1 time of a substance (tissue or other substance) type that is of no interest in the contrast agent-enhanced magnetic resonance image of the subject region. The T1 time of this substance type is determined from the pre-measurement. An inversion time T1 for the following contrast agent-enhanced measurement is calculated from this T1 time as T1=ln2×T1 and is utilized in the following measurement.

As used herein a "tissue type" or "substance type" means any constituent of the subject region of interest that can be discriminated by means of the T1 time, for example bone mass, a specific muscle tissue, blood or fat.

The T1 time of the tissue or substance type that should appear dark in the subsequently produced MR image is determined by the pre-measurement immediately before each measurement of a specific measurement time after administration of the contrast agent. Given knowledge of this T1 time, the T1 time for the measurement at which this tissue type or substance type supplies no signal contribution in the MR image then can be exactly calculated. This corresponds to the relationship T1 =ln2×T1. The same pre-measurement can be implemented in further measurements at a later point in time at which the T1 of the tissue type or substance type, for example healthy heart musculature, that is of no interest has changed because the contrast agent has been flushed out. The T1 time required for an optimum contrast thus is also exactly calculated and utilized for the measurement at these further points in time.

In this way, it is no longer necessary to utilize empirical values for the T1 and respectively adapt them during the dynamic measurement. On the contrary, the T1 required for an optimum image contrast is always determined and utilized. This leads to a simpler methodology with qualitatively high-grade MR images.

The present method is well suited for the determination of the myocardium vitality making use of the effect of late enhancement, whereby the tissue type that is of no interest and for which the T1 time is determined represents vital myocardium tissue. This vital muscle tissue at the heart need not be visible in the magnetic resonance images of the dynamic magnetic resonance measurement since it is only the non-vital muscle tissue regions that are to be localized in bright regions or pixels in the image as a result of the late enhancement. An optimum contrast and an optimum recognizability of the dead tissue regions can be realized due to the knowledge of the T1 times of the vital muscle tissue at the individual measurement times as well as the selection of the T1 time resulting therefrom.

For determining the T1 time of the tissue type or substance type that is of no interest, an MR image preferably is generated from the pre-measurement and the tissue type or substance type of no interest is marked in this image. As a result of this marking, the determination of the T1 time can be limited to the specifically selected tissue or substance type.

The pre-measurement for determining the T1 time preferably is implemented as a fast single-shot measurement in order to keep the measuring time and, in particular, the temporal distance of the T1 determination from the following, actual measurement short. Such single-shot measurements for determining the T1 time are well known to those skilled in the art. For example, an inversion recovery True-Fisp sequence can be utilized, as described in K. Scheffler et al., "T1 Quantification with Inversion Recovery TrueFisp", Magnetic resonance in Medicine 45:720–723 (2001).

DESCRIPTION OF THE PREFERRED EMBODIMENTS

Figure 1:
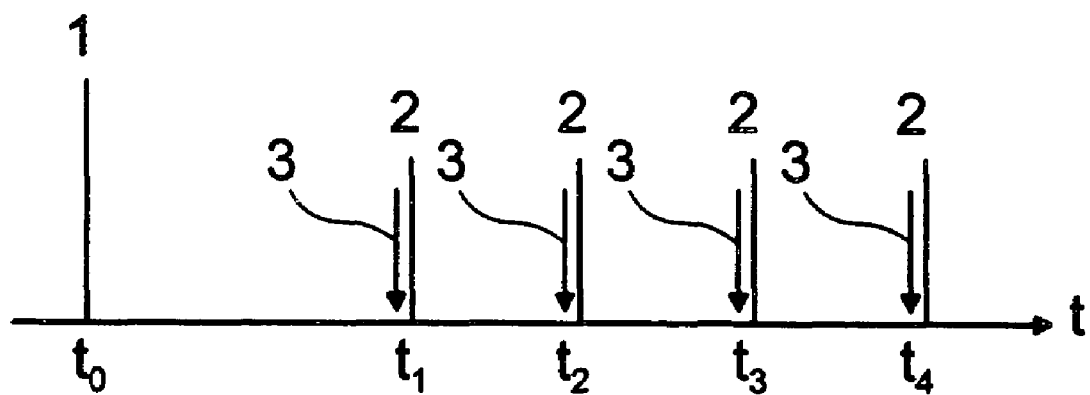
FIG. 1 is a schematic example of the fundamental time sequence of a dynamic magnetic resonance measurement with the application of a contrast agent.

FIG. 1 schematically shows an example of an executive sequence of a dynamic magnetic resonance measurement with the application of a contrast agent on a time axis. At time $t_0$, the patient is thereby injected with a contrast agent that shortens the T1 times (reference character 1). After administering this contrast agent, a specific time duration, for example 5 minutes is allowed to elapse before the first imaging magnetic resonance measurement 2 is implemented at time $t_1$ upon employment of an inversion recovery technique for generating a T1-weighted MR image of the heart. Further such magnetic resonance measurements 2 are implemented in the same way at later times $t_2$–$t_4$ that, for example, can be spaced apart at 2 minute intervals. The late enhancement in a tissue region damaged by an infarction can be observed from the magnetic resonance images acquired at the various points in time $t_1$–$t_4$. The contrast in the respective magnetic resonance images is highly dependent on the T1 time selected in the measurement. The T1 time indicates the time from the application of the 180° pulse of the inversion recovery sequence after which the magnetization is interrogated. By suitably selecting the T1 time in every measurement 2, the contrast in the magnetic resonance image can be optimized, so that, for example, tissue types of no interest such as vital heart muscle tissue supply no signal contribution in the MR image, i.e. appear dark. The condition therefor is that TI =ln2*T1, whereby T1 corresponds to the longitudinal relaxation time of the uninteresting tissue type at this point in time.

In the present method, the T1 time of the uninteresting tissue type is determined before each measurement by a pre-measurement 3, as schematically indicated on the basis of the arrows in FIG. 1. A different T1 of the uninteresting tissue type or a different optimum T1 arises from each pre-measurement 3 because of the dynamic process due to the administration of contrast agent. This T1 is then respectively utilized for the measurement 2 immediately following the pre-measurement 3. Of course, the number of individual measurements 2 during such a dynamic measurement is arbitrary, as is their spacing, and is selected by a person skilled in the art dependent on the existing conditions and the desired results.

Figure 2:
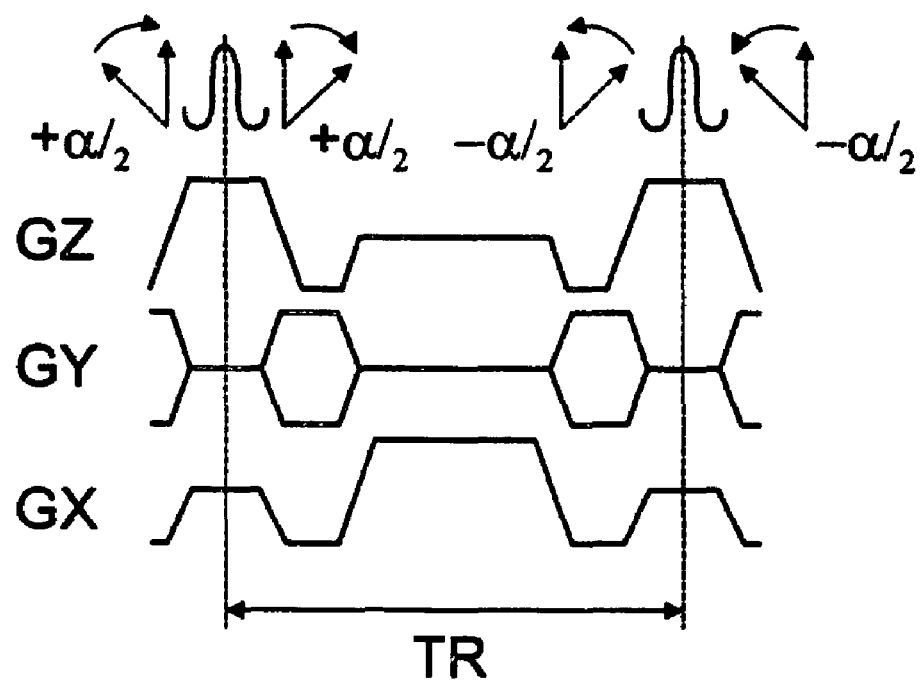
FIG. 2 is an example of a measurement sequence for the implementation of a pre-measurement for determining the T1 time.

An inversion recovery TrueFisp sequence as schematically shown in FIG. 2 is utilized for the implementation of the pre-measurement in the present example. Given this pulse sequence, successive excitation pulses with the flip angle a are applied with alternating polarity. The gradient fields are switched in the illustrated way during a repetition time span TR as shown in FIG. 2, that begins with the center of the +α pulse and ends with the center of the –α. GZ represents the gradient coil for defining the slice, GY the gradient coil for phase coding and GX the gradient coil for the readout direction. The longitudinal magnetization oscillates between +and –α/2 around the Z-axis in this measurement.

Figure 3:
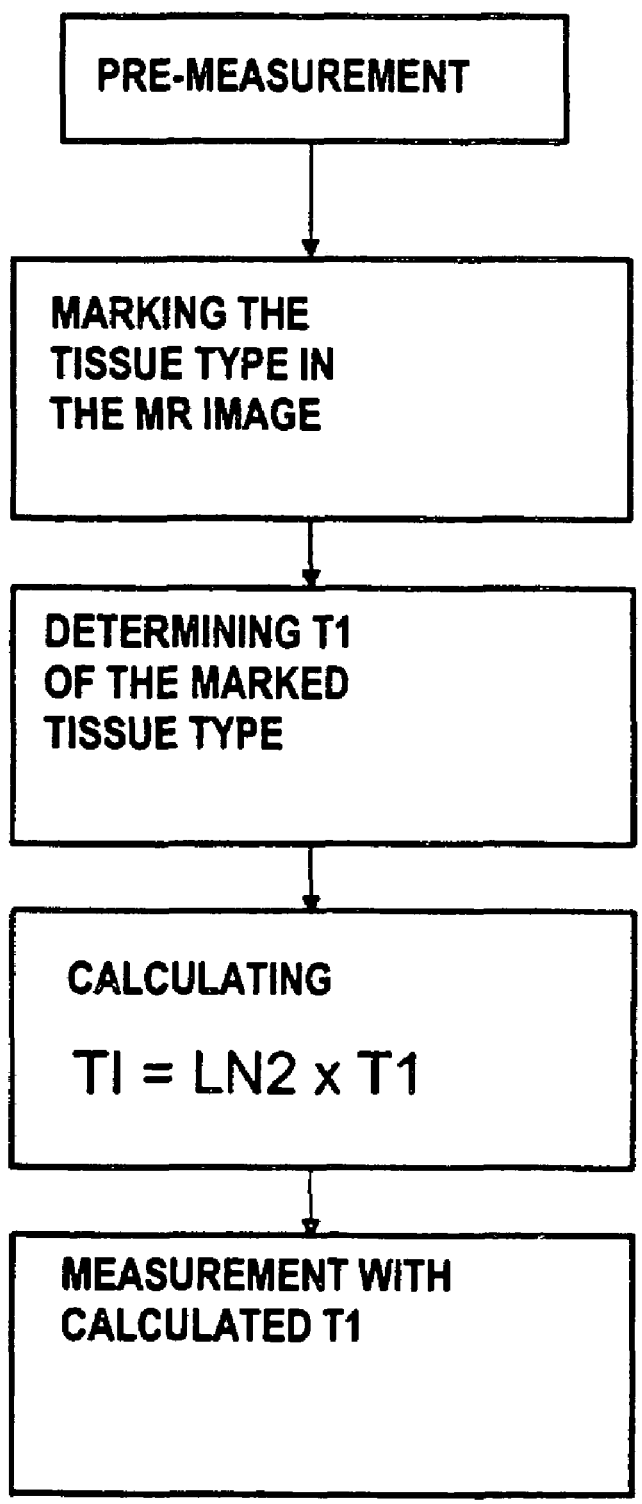
FIG. 3 is a flowchart of the basic steps of the present method.

In an exemplary executive sequence of a dynamic magnetic resonance measurement with an application of contrast agent with an optimization of the T1 time, an overview image of the subject region usually is made first with a magnetic resonance measurement. The subject region to be measured is marked on the basis of this overview image, and the target sequence is set to the desired position. After the administration of the contrast agent and the waiting time following thereupon, a pre-measurement is implemented with an inversion recovery TrueFisp sequence or a similar fast method. The tissue type or tissue region that should appear dark in the following MR images is interactively marked in the MR image generated therefrom. For example, this can be vital heart muscle tissue. After the marking, the T1 value of this tissue type of the marked region is automatically defined from the pre-measurement and a TI time is calculated therefrom with TI =ln2×T1, as can be seen, for example, with reference to the method steps of FIG. 3. The calculated T1 is subsequently handed over to the measurement system for the following measurement and this measurement is started. The imaging MR measurement therefore ensues with the optimum T1 time that supplies the desired contrast in the MR image. An estimate or recourse to empirical values is not required, as is conventionally necessary.

Even though the present description and the exemplary embodiments are referenced to the vitality measurement at the heart, a person skilled in that art also can utilize the present method in other area of employment wherein a dynamic magnetic resonance measurement is implemented with the application of a contrast agent by means of an inversion recovery sequence, and the image contrast should be optimized by blanking out or, respectively, darkening a tissue type or substance type.

Although modifications and changes may be suggested by those skilled in the art, it is the intention of the inventor to embody within the patent warranted hereon all changes and modifications are reasonably and properly come within the scope of his contribution to the art.

I claim as my invention:

1. A method for implementing a dynamic magnetic resonance measurement with application of a contrast agent, comprising the steps of:

administering a contrast agent to an examination subject for subsequently obtaining a first contrast agent-enhanced image of a region of said subject containing a substance type not enhanced by said contrast agent having a T1 time associated therewith;

conducting a pre-measurement of said region, after administration of said contrast agent, with a magnetic resonance sequence to obtain said first contrast agent-enhanced image and identifying said T1 time of said substance type from said first contrast agent-enhanced image of said pre-measurement;

determining an inversion time TI as $\ln 2 \times T1$; and immediately after said pre-measurement, obtaining a second contrast agent-enhanced magnetic resonance image of said region using an inversion recovery sequence with said inversion TI determined from said pre-measurement.

2. A method as claimed in claim 1 comprising obtaining a plurality of contrast agent-enhanced magnetic resonance images of said region, using an inversion recovery sequence, following application of said contrast agent and conducting a respective pre-measurement immediately preceding each of said contrast agent-enhanced magnetic resonance measurements and determining an inversion time T1 after each pre-measurement and using the respective inversion times T1 in the inversion recovery sequences used to obtain the plurality of contrast agent-enhanced magnetic resonance images.

3. A method as claimed in claim 1 comprising the additional step of, from said contrast agent-enhanced magnetic resonance measurement, determining myocardium vitality using the late enhanced effect, and wherein said substance type for which said T1 time is determined is vital myocardium tissue.

4. A method as claimed in claim 1 comprising marking said substance type in said magnetic resonance image obtained in said pre-measurement and determining said T1 time only for the marked substance type.

5. A method as claimed in claim 1 comprising conducting said pre-measurement as a single-shot magnetic resonance measurement.

6. A method as claimed in claim 5 comprising employing an inversion recovery TrueFisp sequence for said pre-measurement.

* * * * *